United States Patent [19]

de Buman et al.

[11] 4,369,784
[45] Jan. 25, 1983

[54] METHOD FOR MAKING SUPPOSITORIES BY COMPRESSION AND PRODUCT OF SAME

[75] Inventors: Alain de Buman, Düdingen; Aldo Riva, Berne; Heinz Sucker, Basel, all of Switzerland

[73] Assignee: Sandoz Ltd., Basel, Switzerland

[21] Appl. No.: 214,747

[22] Filed: Dec. 9, 1980

Related U.S. Application Data

[63] Continuation of Ser. No. 27,427, Apr. 5, 1979, abandoned.

[30] Foreign Application Priority Data

Sep. 29, 1978 [CH] Switzerland .................. 10194/78

[51] Int. Cl.³ .................. A61J 3/08; B29B 3/00; B29C 11/00
[52] U.S. Cl. .................. 128/271; 264/28; 264/117; 264/122
[58] Field of Search .................. 264/28, 109, 117, 122; 128/271; 424/38, 358

[56] References Cited

U.S. PATENT DOCUMENTS

| | | | |
|---|---|---|---|
| 2,307,371 | 1/1943 | Hileman | 264/28 |
| 2,874,417 | 6/1954 | Ramse | 264/297 |
| 4,134,943 | 1/1979 | Knitsch et al. | 264/28 |

FOREIGN PATENT DOCUMENTS 2553026  6/1976  Fed. Rep. of Germany .

OTHER PUBLICATIONS

Thesis of H. J. Meyer, H. J. Meyer, 1974, Meyer Thesis Para 3.3, pp. 158–160.
Sprowl's Amer. Pharm., 7th Ed., 1974.
German Language Abstract, Buman/Riva/Sucker, 4/78.
Golovkin Farmatsevtichnii Zhurnal (Kiiv), 30, 88–89, (1975).
Golovkin et al., Khimiko-Farmatsevticheskii Zhurnal, vol. 11, pp. 115–118, Jun. 1977.

*Primary Examiner*—Willard E. Hoag
*Attorney, Agent, or Firm*—Gerald D. Sharkin; Robert S. Honor; Walter F. Jewell

[57] ABSTRACT

This invention provides a compression process for the production of suppositories characterized in that the compression step is effected at a temperature at or below +10° C., and in the absence of a binding agent.

13 Claims, No Drawings

METHOD FOR MAKING SUPPOSITORIES BY COMPRESSION AND PRODUCT OF SAME

This is a continuation of application Ser. No. 27,427 filed Apr. 5, 1979 now abandoned.

This invention relates to the manufacture of suppositories.

Industrial manufacture of suppositories normally involves a moulding process in which a molten mixture of suppository base and active agent is poured into moulds. This procedure has certain disadvantages, in particular the exposure of the active agent to elevated temperatures at which it may not be stable, the possibility of sedimentation of active agent during the moulding process and the problems that high quantities of active agent may result in a mixture too viscous to pour. To overcome such problems, it has already been proposed to employ a simple compression process, which may be effected on conventional tabletting equipment, employing a mixture or granulate comprising the suppository base, active agent and a binding agent such as polyvinylpyrrolidone or sodium carboxymethylcellulose in a solvent. This process may, however, result in suppositories of unsatisfactory biopharmaceutical or physical properties, e.g. low bioavailability of active agent, cracks and other faults due to air entrapment etc.

Some at least of these disadvantages are attributable to the presence of the binding agent. For example, the presence of binding agents such as polyvinylpyrrolidone may raise the drop point of the resulting suppositories to unsatisfactorily high levels and result in inadequate or inconsistent release of active agent.

It has now been surprisingly found that compressed suppositories may be produced without binding agents if the compression step is effected at sufficiently low temperatures.

The invention accordingly provides in one aspect a compression process for the production of suppositories characterized in that a suppository base and a pharmacologically active agent are compressed at a temperature of 10° C. or below, in the absence of an added binding agent.

The preferred press temperature will naturally depend on the particular suppository mass and pharmacologically active agent used. It should not be so high that the suppositories begin to stick to the die. In general, the temperature is preferably below +5° C. and especially at or below 0° C. Preferably the press temperature is at or above −5° C. and generally at or above −10° C.

Additionally the humidity of the atmosphere around the suppository mass should be adjusted to avoid water condensation or ice formation at the room and press operating temperature. It may be from 5 to 50% relative air humidity. The preferred value may be ascertained by means of a Mollier diagram (see Sucker, Fuchs and Speiser, "Pharmazeutische Technologie", Georg Thieme Verlag, Stuttgart 1978).

The press may be a coventional single die press or preferably a multi-die press, e.g. rotary press. This rotary press may be a conventional tabletting press fitted with suitably shaped dies and adapted so that any heat developed during the punch cycle is substantially eliminated and the temperature of the mass being pressed remains at below 10° C., and also adapted so that the relative humidity of the atmosphere around the mass being pressed may be adjusted. If desired, the press may be a high-speed press, e.g. capable of producing more than 50,000 suppositories per hour. Thus the press may be provided with means for maintaining the suppository die at a temperature of 10° C. or below and preferably humidity control.

Additionally, conveniently cooling means are provided for the feed hopper and any stirring blade present.

Conveniently die surfaces and punches are coated with a polymer such as a perfluorinated hydrocarbon e.g. TEFLON (registered trade mark) to minimise adhesion.

As used hereinafter, "conventional suppository bases" refers to the following listed bases alone or in combination. Such bases may be hard fats, e.g. mono-, di- and tri-glycerides of saturated straight chain fatty acids (e.g. $C_{10}$ to $C_{18}$). Examples of those found to be suitable are:

Witepsol (Registered Trade mark), e.g. Witepsol H 15 available from Dynamit Nobel, W. Germany. Suppocire (Registered Trade Mark), e.g. Suppocire AM or AS2, available from Gattefosse, France. Novata (Registered Trade Mark), e.g. Novata BD, available from Henkel GmbH, W. Germany. Alternatively, the Guerbet alcohols may be used.

As indicated above the process according to the invention is effected in the absence of a binding agent, e.g. cellulose derivatives, and polymers such as polyvinylpyrrolidone (see Fiedler, Lexikon der Hilfsstoffe, Editio Cantor 1971, p. 556 for other examples).

The suppository mass to be pressed may for example be produced by dry granulating processes. The granulate may for example be made by pressing the mass through a sieve of mesh width of from 0.5 to 2 mm. A powdered suppository base and the pharmacologically active agent, optionally in powdered form, may be mixed in a vessel cooled by cold water, over a period of about 15 minutes. Then the mixture may be kneaded by warming the vessel with warm water at about 40°, whereupon generally large lumps of material are formed within a short time. The lumps are generally then at a temperature of about 28° to 30° C. They are then cooled to about 4° C. and granulated.

Alternatively, about 70 to 90% of the weight of the necessary powdered suppository base may be mixed with the powdered pharmacologically active agent in a kneading machine. The remaining suppository base may be melted and warmed to about 45° C. and then kneaded with this material. In a few minutes a compact mass of large lumps is formed. This may be cooled to about 4° C. and granulated. As used hereinafter "melt granulation" refers to this alternate method.

Alternatively the suppository base may be granulated along the lines indicated above in the absence of the pharmacologically active agent which is then finally mixed into the granulate.

In a further method, the suppository base in the form of large lumps may be ground to a diameter of less than 2 mm and then mixed with the pharmacologically active agent.

The suppositories made according to the present invention may contain any pharmacologically active agent which may be administered by the rectal, vaginal, or uretheral route. Such active agents include antirheumatics, anti-biotics, anti-asthmatics, anti-histamines, spasmolytics, sedatives, vasodilators, analgesics, tranquillizers, and anti-inflammatories. Examples of compounds which may be used as active agents include the ergot alkaloids, e.g. ergotamine and dihydroergotamine, other alkaloids, e.g. belladonna, barbituate derivatives such as butalbital, phenazone derivatives such as propyphenazone, acetylsalicylate derivatives, e.g. calcium or sodium acetylsalicyclate, digitalis derivatives, e.g. lanatoside C, caffeine, thiethylperazine, tropenzilium bromide, piperylone, quinazoline derivatives such as proquazone, etc.

The amount of active agent pressed will naturally depend on its effective dose, the rate of absorption, and the suppository mass. In general, a suppository made according to the invention may contain up to 450 mg of active agent per gram suppository total weight.

The following examples illustrate the invention. All temperature are in degrees Centigrade. Each suppository weighs 2 g, except where otherwise stated.

EXAMPLE 1

18.75 kg propyphenazone, 7.5 kg butalbital and 3.75 kg anhydrous caffeine are mixed, passed through a sieve of 0.3 mm mesh width and then stirred for ten minutes together with 70 kg powdered Witepsol H 15 in a kneading machine fitted with a cooling mantel through which cold water is passed. The temperature of the water is raised to 40° C. and the mixture is formulated over 10 minutes into large lumps having a final temperature of 28° to 30° C. The warm mass is taken out of the kneading machine and is cooled to 4° C. The cold mass is granulated using a sieve of 1.6 mm mesh width. The granulate is compressed into suppositories in a rotary press at a temperature of from −10° C. to +50° C. at a rate of 100,000 suppositories per hour.

EXAMPLE 2

30 kg proquazone and 55 kg powdered Witepsol H 15 are mixed in a kneading machine. This mass is kneaded with 15 kg of molten Witepsol H 15 (temperature about 40°-45°) over 15 minutes. The mass is cooled to 4° and granulated using a sieve of 1.6 mm mesh width. The granulate is compressed as in Example 1 at a temperature of from −10° to 0° at a rate of 60,000 suppositories per hour.

EXAMPLE 3

18.75 kg propyphenazone, 7.5 kg butalbital, 6 kg anhydrous caffeine, 0.08 kg dihydroergotamine and 67.65 kg Witepsol H 15 are granulated and compressed as described in Example 1 at a rate of 80,000 suppositories per hour.

EXAMPLE 4

This is effected in analogous manner to Example 1 using Suppocire AS2 instead of Witepsol H 15. Compression rate 80,000 suppositories per hour.

EXAMPLE 5

39.6 kg calcium acetyl salicyclate and 60.4 kg Witepsol H 15 are granulated and compressed at a rate of 60,000 suppositories per hour in analogous manner to Example 1.

EXAMPLE 6

15 kg proquazone and 85 kg Novata BD are granulated and compressed in analogous manner to Example 1 at a rate of 70,000 suppositories per hour.

EXAMPLE 7

18.75 kg propyphenazone, 7.5 kg butalbital and 3.75 kg anhydrous caffeine are mixed, sieved (mesh width diameter 0.25 mm) and mixed with 50 kg Witepsol H 15. This mixture is kneaded with 20 kg molten Witepsol H 15. The mass is formulated into large lumps. The warm mass is worked up further as described in Example 1 and compressed finally into suppositories at a rate of 60,000 per hour.

EXAMPLE 8

0.105 kg Ergotamine tartrate, 1 kg tartaric acid and 2.926 kg lactose are mixed and pressed through a sieve of 0.25 mm mesh width. Separately 0.0223 kg Belladonna, 5 kg butalbital, 0.0062 kg malic acid, and 5.15 kg anhydrous caffeine are mixed and passed through a sieve of 0.35 mm mesh width. Both mixtures are mixed in a kneading machine with 84.7905 kg Suppocire AM and worked up further as in Example 1, finally being compressed into suppositories, each weighing 1.95 g, at a rate of 60,000 per hour at −10° C. to 0° C.

EXAMPLE 9

70 kg Witepsol H 15 is granulated as in Example 1 without the addition of any active agents. The resulting granulate is mixed with 30 kg proquazone in a mixer and compressed at −10° to 0° C. to produce 50,000 suppositories per hour.

EXAMPLE 10

1.875 kg propyphenazone, 0.75 kg butalbital and 0.375 kg anhydrous caffeine are passed through a sieve of 0.35 mm mesh width, mixed with 7 kg Witepsol H 15 which has been ground and passed through a mesh of 0.7 mm mesh width, and compressed at a temperature of from −10° to 0° at a rate of 50,000 suppositories per hour.

What we claim is:

1. A compression process for the production of a suppository comprising forming a granulate mixture of a conventional suppository base and a pharmacologically active agent, said mixture being free from added binder, and compressing said mixture while maintaining said mixture at a temperature not greater than 10° C.

2. A compression process according to claim 1 wherein the temperature is at or below +5° C.

3. A compression process according to claim 2 wherein the temperature is from −10° to 0° C.

4. A compression process according to claim 1 wherein a suppository base is a hard fat suppository base.

5. A compression process according to claim 1 wherein the pharmacologically active agent is an ergot alkaloid.

6. A suppository whenever produced by a compression process according to claim 1.

7. The process according to claim 1 wherein the suppository base and the pharmacologically active agent and first granulated together before being compressed.

8. The process according to claim 1 wherein an inert filler material is incorporated in the suppository.

9. Process of claim 1, in which the granulate is obtained by
    subjecting a mixture containing the suppository base and the pharmacologically active agent to a dry granulation process.

10. The process according to claim 1 wherein an inert filler material is incorporated in the suppository.

11. Process of claim 1, in which the granulate is obtained by subjecting at least a part of the suppository base to a melt granulation process and mixing the cooled suppository base in granulate form with the pharmacologically active agent and with the rest of the suppository base.

12. A process of claim 1 effected on a high speed rotary die press tabletting machine.

13. Process of claim 12, in which at least 50,000 suppositories per hour are produced.

* * * * *